(12) United States Patent
Nijenbanning et al.

(10) Patent No.: US 8,096,991 B2
(45) Date of Patent: Jan. 17, 2012

(54) MEDICAL DEVICE FOR TREATING BROKEN BONES OR FIXING STABILISING ELEMENTS TO BONE PARTS

(75) Inventors: Gert Nijenbanning, Hengelo (NL); Ariaan Dirk Pieter Van Walsum, Enschede (NL)

(73) Assignees: Beat Holding B.V., Hengelo (NL); Corpus Liberum B.V., Enschede (NL)

( * ) Notice: Subject to any disclaimer, the term of this patent is extended or adjusted under 35 U.S.C. 154(b) by 798 days.

(21) Appl. No.: 12/090,447

(22) PCT Filed: Oct. 17, 2006

(86) PCT No.: PCT/NL2006/000523
§ 371 (c)(1),
(2), (4) Date: Jul. 9, 2008

(87) PCT Pub. No.: WO2007/046691
PCT Pub. Date: Apr. 26, 2007

(65) Prior Publication Data
US 2008/0262497 A1    Oct. 23, 2008

(30) Foreign Application Priority Data
Oct. 18, 2005   (NL) .................................. 1030218

(51) Int. Cl.
*A61B 17/56*   (2006.01)

(52) U.S. Cl. .......................................... 606/63; 606/62
(58) Field of Classification Search ............. 606/63–68, 606/74, 75, 232
See application file for complete search history.

(56) References Cited

U.S. PATENT DOCUMENTS

| | | | |
|---|---|---|---|
| 6,224,600 B1 * | 5/2001 | Protogirou ..................... | 606/63 |
| 6,328,758 B1 | 12/2001 | Tornier et al. | |
| 7,052,498 B2 * | 5/2006 | Levy et al. ..................... | 606/63 |
| 2003/0078581 A1 * | 4/2003 | Frei et al. ...................... | 606/68 |
| 2004/0133204 A1 | 7/2004 | Davies | |

FOREIGN PATENT DOCUMENTS

| | | |
|---|---|---|
| EP | 1254639 A | 11/2002 |
| FR | 2653006 A | 4/1991 |

* cited by examiner

*Primary Examiner* — Pedro Philogene
(74) *Attorney, Agent, or Firm* — Muncy, Geissler, Olds & Lowe, PLLC (57) ABSTRACT

A medical device for fixing bone parts or for fixing stabilizing elements to bone parts. A rigid outer tube is provided with at least two opposed recesses on the side that is positioned in the bone. A second inner tube is accommodated in the rigid outer tube. The inner tube is provided with at least two strips extending in the longitudinal direction of the inner tube on the side that is positioned in the bone. The medical device is provided with a device for loading the inner tube in the axial direction, in such a manner that a pressure force is exerted on the strips, which pressure force causes the strips to bend outwards through the recesses.

9 Claims, 6 Drawing Sheets

MEDICAL DEVICE FOR TREATING BROKEN BONES OR FIXING STABILISING ELEMENTS TO BONE PARTS

FIELD OF THE INVENTION

The present invention relates to a medical device suitable for fixing bone parts, comprising a rigid outer tube, which is provided with at least two opposed recesses near the first end that is positioned in the bone, an inner tube that can be accommodated in the rigid outer tube, which inner tube is provided with at least two strips extending in the longitudinal direction of the inner tube on the side that is positioned in the bone, as well as means for loading the inner tube in axial direction, in such a manner that a pressure force exerted on said strips causes the strips to bend outwards through the aforesaid recesses, which means for loading the inner tube in axial direction are made up of a screw that fits in another end of the outer tube that is positioned in the bone, which screw mates with screw thread present on the inner wall of the outer tube, wherein the first end of the outer tube that is positioned in the bone is made to exert a pressure force on the outwardly bending strips by suitably turning the screw.

BACKGROUND OF THE INVENTION

Medical devices of the kind to which the present invention relates are used in positioning bone parts with respect to each other in case of a fracture or if two bones that are connected via one or more joints are to be immobilised. In all these cases the medical devices of the present kind are intended to take up and transmit a load in a direction substantially transversely to the longitudinal direction of the medical device.

Medical devices intended for fixing broken bone parts relative to each other are used in particular in the treatment of a broken femur head. An example of known medical devices of this kind is to be found in European patent EP 0 337 288 A1. According to said document, one or more screws are screwed into the femur head, which screw is slidingly (in only one direction) accommodated in the plate that is fixed to the femur by means of screws. The screw and the plate are rigid, to such an extent that the device is capable of transmitting loads resulting from walking movements in a direction transversely to the longitudinal axis of the screw, wherein the screw can move at a fixed angle in the direction of the femur, as a result of which the broken bones are firmly pressed together in the plane of fracture.

Another example of the known medical devices is to be found in U.S. Pat. No. 0,004,514 A1, for example, which employs a pin that is placed in the intramedullary cavity of the upper leg. A problem that occurs with these known devices is caused by the fact that the femur head can rotate freely about the screw axis with respect to the screw, in any case during insertion, which may lead to necrosis of the femur head. In addition, placement of the screw may cause damage to the bone in the femur head, to such an extent that it seriously impedes the healing process.

Medical devices that attempt to obviate this problem are known from U.S. Pat. No. 3,561,437, in which the pin is slidingly accommodated in one direction in the plate and the pin is driven rather than screwed into the bone. A problem that occurs with these known devices is caused by the fact that the pin can easily move out of the femur head.

To obviate this problem, constructions consisting of a pin that is slidingly accommodated in a plate have been conceived, in which constructions the pin is provided with elements that can expand in a direction transversely to the longitudinal direction of the pin. Examples of such constructions are shown in U.S. Pat. Nos. 2,699,774, 2,397,545 and 4,204,531, for example. With all these constructions, the end of the pin that faces towards the femur head is provided with elements that are movable in the transverse direction of the pin, which parts elements are moved apart by suitable means once the pin has been placed. All these suitable means are fairly complicated and thus costly. A drawback of these known devices is that they are not hollow, so that they cannot be inserted over a guide wire.

Medical devices intended for use in situations in which two bones connected by a joint are to be immobilised are used in particular in fixing a vertebral segment. An example of known medical devices of this kind is to be found in U.S. Pat. No. 5,209,753, in which a screw is inserted into the pedicles of two or more vertebrae, which vertebrae are connected by means of plates or rods.

A problem that occurs with these known devices is caused by the fact that part of the bone in the pedicle may be damaged, to such an extent that a proper fixation is not obtained. In addition, very dangerous situations may arise upon turning a screw into the vertebra, because fibres of the dura may get entangled when the screw breaks through the pedicle wall on the side of the spinal cord.

SUMMARY OF THE INVENTION

The object of the present invention is to provide a device that can be used for positioning bone parts or for connecting stabilising means to bone parts on either side of a joint so as to immobilise the intermediate joint, which device is sufficiently rigid for transmitting loads being exerted on the bone parts as a result of certain postures and movements of the body in a direction substantially transversely to the longitudinal axis of the device, without there being a risk of the medical device being driven out of the bone, and which can be inserted over a guide wire by simple surgery.

In order to accomplish the above object, the medical device according to the invention is configured as a rigid outer tube, which is provided with at least two opposed recesses on the side that is positioned in the bone, wherein a second inner tube is accommodated in said rigid outer tube, which inner tube is provided with at least two strips extending in the longitudinal direction of the inner tube on the side that is positioned in the bone, whilst means are present for loading the inner tube in axial direction, in such a manner that a pressure force is exerted on the aforesaid strips, which causes said strips to bend outwards through the aforesaid recesses.

In this way the device is capable of transmitting loads, such as transverse forces and bending moments, in a direction transversely to the longitudinal axis of the device, whilst the device is nevertheless secured against movement in the direction of its longitudinal axis. In this way the device is locked against being driven out of the bone part in question.

According to the invention, the means for loading the inner tube may be formed by a screw that fits in the outer tube, which screw mates with screw thread present on the inner wall of the outer tube, wherein the end piece, in this case made up of a shoulder, can exert a pressure force on the strips, causing said strips to bend outwards, by suitably turning the screw.

Another advantageous embodiment of the device according to the invention is characterised in that the inner tube is connected to the screw, which tube and which screw are hollow. The advantage of this is that the device as a whole can be inserted over a guide wire, which is especially important in the case of minimally invasive surgical procedures.

According to another embodiment, the means for loading the inner tube are formed by a sleeve, which is provided with screw thread on its outer wall, which screw thread mates with screw thread on the inner wall of the outer tube. The sleeve is further connected to the inner tube, in such a manner that the sleeve can only rotate about the longitudinal axis of the inner tube with respect to the inner tube. By suitably rotating the sleeve, a pressure force will be exerted on the strips of the inner tube, so that the strips will bend outwards through the recesses in the outer tube.

According to the invention, the connection between the inner tube and the sleeve may be formed by an annular wire, which is accommodated in a recess jointly formed by a groove in the inner circumference of the sleeve and the outer circumference of the inner tube.

In an advantageous embodiment, the connection between the outer tube and the inner tube may be formed by an annular wire, which is accommodated in a recess jointly formed by a groove in the inner circumference of the outer tube and the outer circumference of the inner tube. In this way the outer tube can be secured in axial direction with respect to the inner tube (i.e. the longitudinal direction of the two tubes), and the inner tube can transmit an axial pressure force to the outer tube, which force is necessary in order to cause the aforesaid strips to bend outwards under plastic deformation.

In this way a simple, inexpensive, strong yet small-sized connection between the inner tube and the sleeve comprising hardly any moving parts is realised, wherein the sleeve can only rotate about the common longitudinal axis with respect to the inner tube.

According to another embodiment, the strips comprise a weakened portion at the location of their centre, seen in the longitudinal direction of the strips. This ensures that the bending of the strips will take place symmetrically relative to their centre. According to the invention, said weakened portion may be formed by an indentation or by one or more holes.

In another advantageous embodiment, the outer wall of the outer tube comprises at least one or more upright sections, which prevent rotation of the broken bone part with respect to the other part of the bone. The medical device according to the invention can be used in particular for treating broken hip-bones according to any one or more of the preceding claims, and is characterised in that the side that is not positioned in the bone is slidingly accommodated in a receiving device, which receiving device is connected at an angle to a plate that can be fixed to a part of the broken hipbone, and in that the side that is positioned in the bone is fixed in the other part of the broken hipbone.

In this way the medical device can take up loads substantially transversely to the longitudinal axis of the device and transmit them to the plate, whilst the device that is positioned in the broken part of the hipbone can slide along the longitudinal axis of the medical device towards the other part, as a result of which the two parts are pressed firmly together, which is very conducive to the healing process. In another advantageous embodiment, the side of the medical device that is not positioned in the bone is slidingly accommodated in an opening of a pin which is placed in the intramedullary cavity of the upper leg.

The medical device according to the invention can furthermore be used in particular for immobilising two bones connected by one or more joints, in particular vertebrae, according to any one or more of the preceding claims, and is characterised in that the pin is connected to stabilising elements on the side that is not positioned in the bone, whilst the part that is positioned in the bone is inserted into the pedicle of the vertebra.

In addition to a medical device as described above, the present invention also relates to a pin which is in particular suitable for use in the above-described device. According to the invention, said pin is characterised in that it is provided with one or more or expandable elements in the form of one or more elongated strips extending in the longitudinal direction of the pin, whilst furthermore means are provided for exerting a pressure force on said strips in the longitudinal direction thereof, causing said strips to bend outwards under plastic deformation in a direction transversely to the longitudinal direction of the pin. The pin according to the invention may furthermore comprise all the features that have been described above upon use thereof in the medical device according to the present invention.

The present invention further relates to a hollow tube provided with two or more strips, which is suitable for use in a medical device or pin as described above.

Furthermore it is advantageous if the outer circumference of the pin according to the invention corresponds to the shape of a hole in the plate, wherein the outer circumference is so configured that the pin can only move in one direction with respect to the plate.

BRIEF DESCRIPTION PF THE DRAWINGS

The invention will now be explained in more detail with reference to the appended drawing, which schematically shows by way of example a medical device with a few embodiments of pins according to the invention that can be used therein.

DETAILED DESCRIPTION OF THE DRAWINGS

Figure 1:
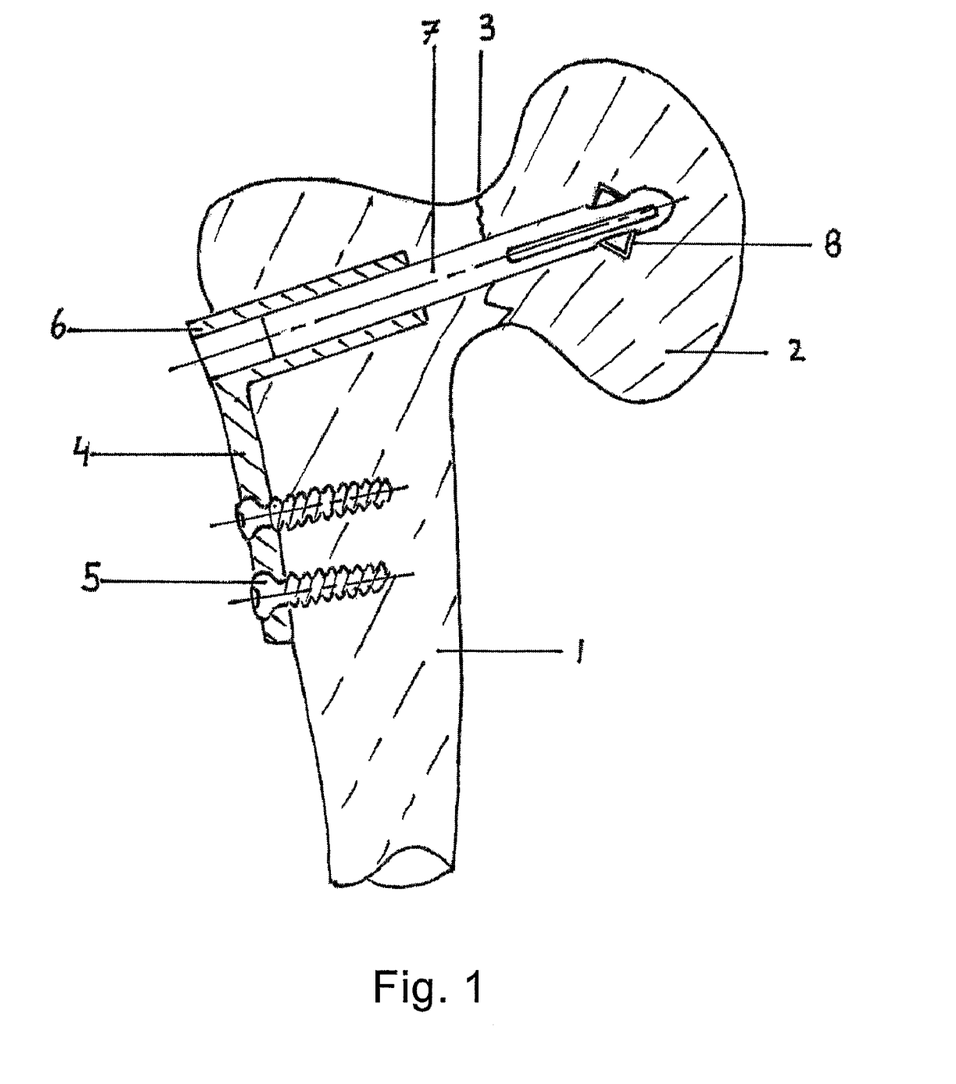
FIG. 1 is a schematic view, not to scale, of a medical device of the kind to which the present invention relates, which shows the device in a situation of use on a broken femur, in which the medical device is slidingly accommodated in a plate.

In FIG. 1, numeral 1 indicates a femur with a femur head 2, whilst numeral 3 indicates a fracture between the femur head and the femur. A plate 4 is fixed to the femur 1 by means of screws 5. The plate 4 is provided with a receiving part 6 including an angle therewith, in which a pin 7 provided with expanded lateral elements 8 is slidingly accommodated.

Figure 2:
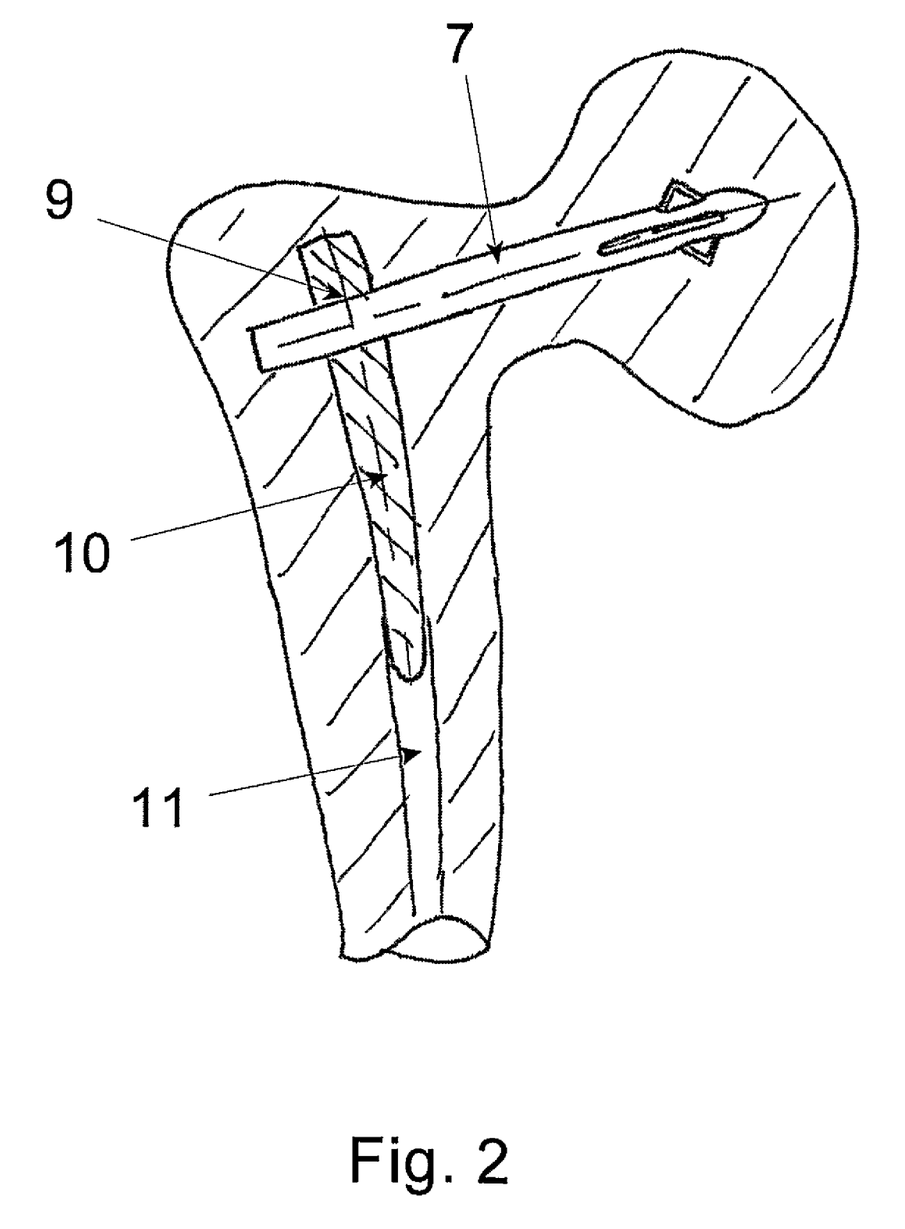
FIG. 2 is a schematic view, not to scale, of a medical device of the kind to which the present invention relates, which shows the device in a situation of use on a broken femur, in which the medical device is slidingly accommodated in a pin that is placed in the intramedullary cavity of the upper leg.

FIG. 2 shows another construction, in which the pin 7 is slidingly accommodated in a cavity 9 of a pin 10 that is positioned in the intramedullary cavity 11 of the femur.

Figure 3:
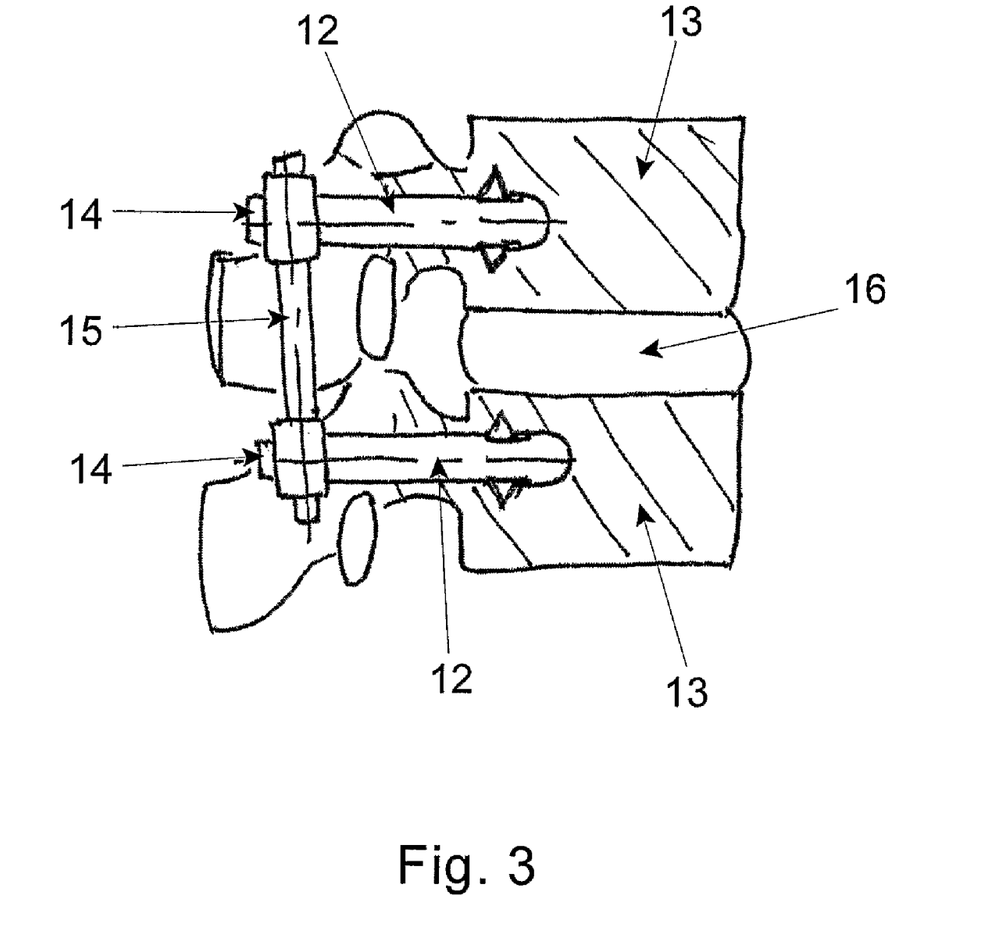
FIG. 3 is a schematic view, not to scale, of a medical device of the kind to which the present invention relates, which shows the device in a situation of use for stabilising a joint between two vertebrae, in which the medical device is positioned in the pedicles of the vertebrae located adjacent to the joint and in which a stabilising element is connected to the two medical devices that are positioned one above another.

FIG. 3 shows a construction comprising two pins, which pins are positioned in pedicles 12 of two vertebrae 13 disposed one above another. A stabilising element 15 is placed between the two pins on the side 14 not positioned in the bone, which element functions to restrict movement of the intervertebral disc 16 between the vertebrae.

The construction and the operation of the medical device will now be discussed in more detail with reference to the following figures. In FIGS. 1, 2 and 3 the expanded elements 8 ensure that a reliable connection that will not come loose is obtained between the medical device and the surrounding bone.

In FIGS. 4-10 an advantageous embodiment of the pin according to the invention is shown.

Figures 4, 5, 6, 7, 8, 9:
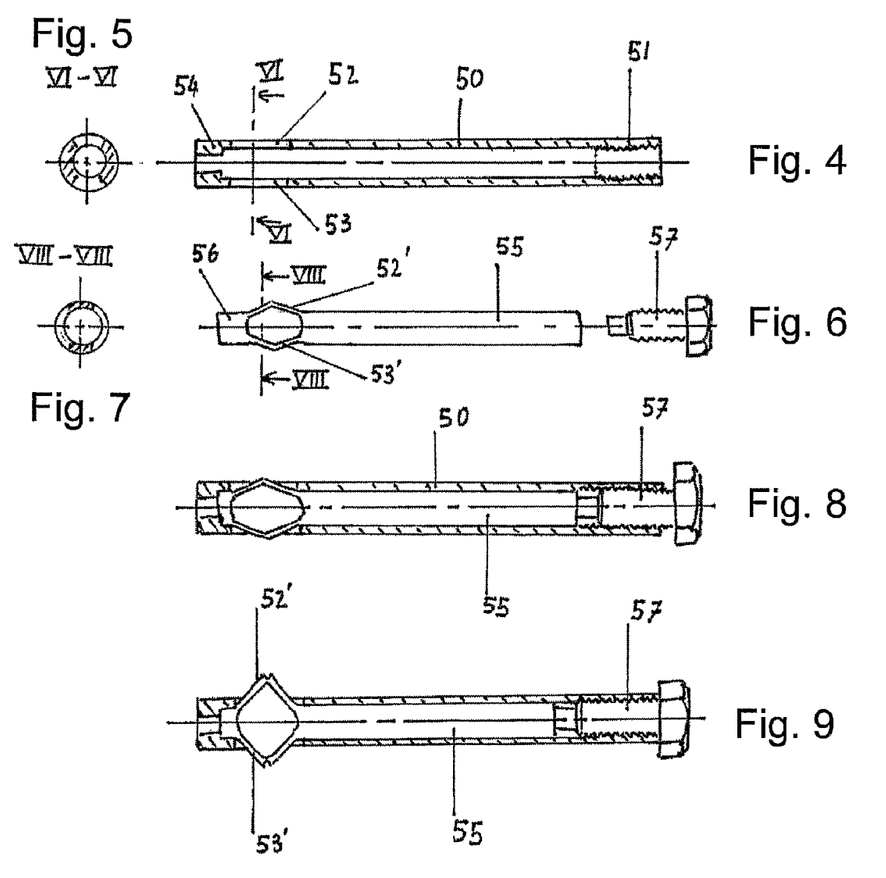
FIGS. 4 and 5 are a schematic, axial cross-sectional view and a schematic sectional view along the line VI-VI, respectively, of an outer, hollow element according to the invention that can be used in the medical device.
FIGS. 6 and 7 are a schematic, axial cross-sectional view and a schematic sectional view along the line VIII-VIII, respectively, of an inner tube that can be accommodated in the inner, hollow element.
FIGS. 8 and 9 are schematic, axial cross-sectional views of the medical device assembled from the parts shown in FIGS. 6 and 7 and the assembled medical device in its situation of use, respectively.

FIG. 4 is an axial cross-sectional view of an outer tube 50, which is provided with screw thread 51 on one side and with recesses 52 and 53 and a shoulder 54 on the other side. FIG. 5 is a sectional view along the line VI-VI of an advantageous embodiment of the outer tube.

FIG. 6 shows an inner tube 55 which is provided with strips, two strips 52' and 53' in this case, on one side, which strips are dimensioned to fit in the recesses 52 and 53 of the outer tube 50 as discussed above. Said strips 52' and 53' are connected by an end piece 56, although said end piece may also be left out under certain circumstances. On the other side a screw 57 is shown, which screw can mate with the screw thread 51. The strips 52' and 53' are already slightly bent in this embodiment, which slightly facilitates the subsequent deformation thereof. FIG. 7 is a sectional view along the line VIII-VIII of an advantageous embodiment of the outer tube.

FIG. 8 schematically shows how the tube 55 can be accommodated in the tube 50 and be sealed by the screw 57. Tightening the screw 57 will result in the inner tube 55 being forced to the left, seen in the drawing, with the end piece 56 thereof abutting against the shoulder 54, as a result of which a pressure force will the exerted on strips 52' and 53', causing them to bend outwards under plastic deformation to the shape shown in FIG. 9. If, for whatever reason, the pin needs to be removed after some time, this can be done by carefully dislodging the pin and retracting it, with the strips partially or entirely deforming back to their original shape. It is possible in this context to connect the screw 57 to the tube 55 in such a manner that the tube 55 is carried along with the screw when the screw is turned back, which will be accompanied, of course, by deformation of the strips 52' and 53' in reverse direction.

In all the preceding examples pins provided with two expandably deformable strips have been shown, but it will be apparent to those skilled in the art that said number may be increased as required.

Figure 10:
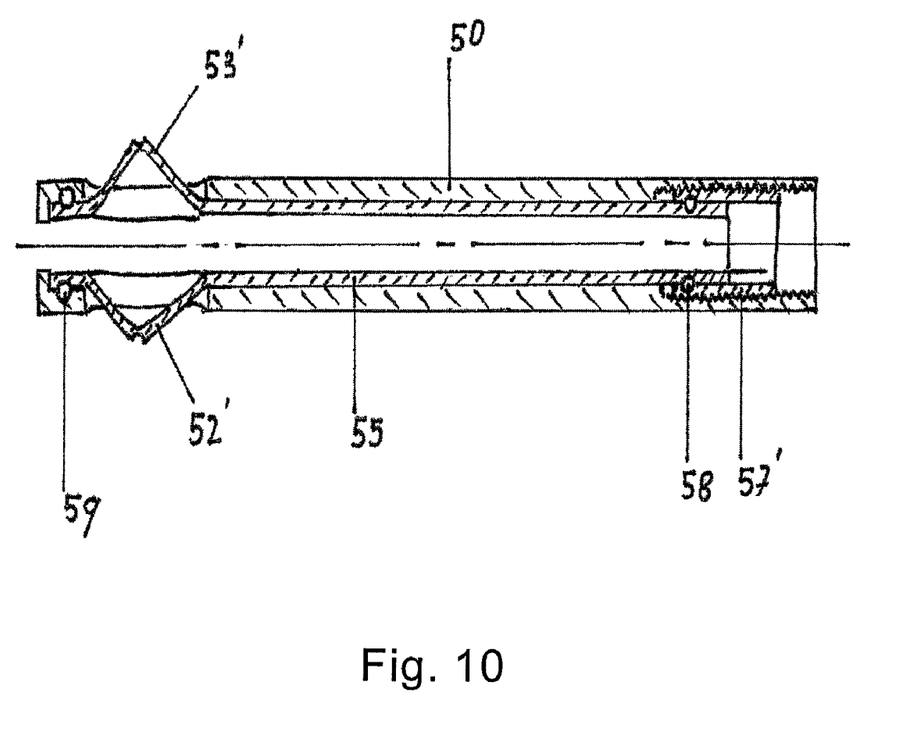
FIG. 10 is a schematic, axial cross-sectional view of another advantageous embodiment of the medical device.

FIG. 10 shows an embodiment in which the connection between the inner wall of the outer tube 50 and the outer wall of the inner tube 55 is formed by an annular wire 59, which functions to fix the two parts in axial direction with respect to each other. A second ring 58 is provided between the outer wall of the inner tube and the hollow sleeve 57' for the purpose of fixing the inner tube and the sleeve in axial direction with respect to each other, the two parts can freely rotate about their common longitudinal axis relative to each other, however. This construction makes it possible to turn the sleeve in or out as desired by means of the mating screw thread 51', as a result of which the strips 52' and 53' will be plastically deformed in inward or outward direction, respectively.

Figure 11:
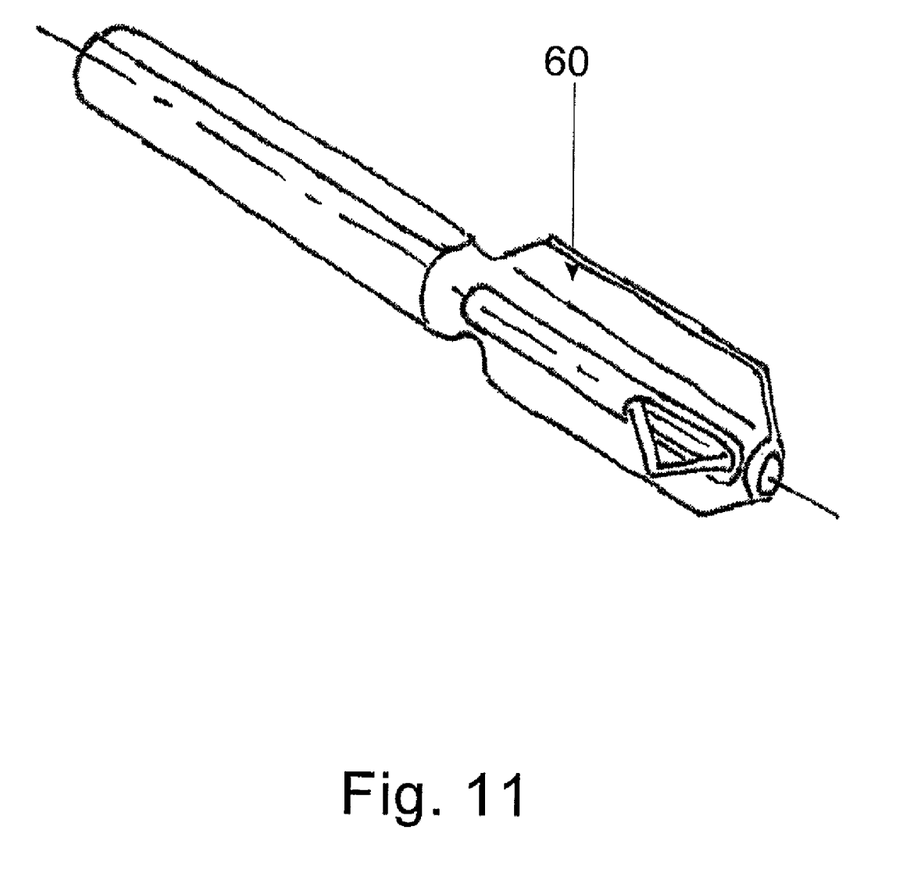
FIG. 11 is a three-dimensional view of an advantageous embodiment of the medical device.

FIG. 11 is a three-dimensional view of an advantageous embodiment of the medical device, which is provided with two wings 60 on the side that is positioned in the bone.

It will be apparent from the foregoing that the invention provides a medical device, and a pin in particular suitable for use therein, for the treatment of broken bones which is remarkable for its simplicity, the absence of mechanical pivot points, its reliability, its ease of use and its relatively low manufacturing costs. Although two embodiments have been discussed in the foregoing, it will furthermore be apparent that many variants are conceivable within the scope of the present invention.

The invention claimed is:

1. A medical device suitable for fixing bone parts, comprising
a rigid outer tube, which is provided with at least two opposed recesses near the first end positioned in the bone,
an inner tube that can be accommodated in the rigid outer tube, which inner tube is provided with at least two strips extending in the longitudinal direction of the inner tube on the side that is positioned in the bone, as well as
means for loading the inner tube in axial direction, in such a manner that a pressure force exerted on said strips causes the strips to bend outwards through the aforesaid recesses, which means for loading the inner tube in axial direction are made up of a screw that fits in another end of the outer tube that is positioned in the bone, which screw mates with a screw thread present on the inner wall of the outer tube, wherein the first end of the outer tube that is positioned in the bone is arranged to exert a pressure force on the outwardly bending strips by suitably turning the screw, characterised in that the connection between the outer tube and the inner tube is formed by an annular wire, which is accommodated in corresponding grooves formed in the inner wall of the outer tube and the outer wall of the inner tube.

2. The medical device according to claim 1, characterised in that the inner tube is connected to the screw, which screw is hollow.

3. The medical device according to claim 1, characterised in that the connection between the screw and the inner tube is formed by an annular wire, which is accommodated in corresponding grooves in the outer wall of the inner tube and the inner circumference of the screw.

4. The medical device according to claim 1, characterised in that said strips comprise a weakened portion at the location of their centre, seen in the longitudinal direction of the strips.

5. The medical device according to claim 4, characterised in that said weakened portion is formed by a cut, an indentation or one or more holes.

6. The medical device according to claim 1, characterised in that the outer tube is provided with one or more upright sections.

7. The medical device according claim 1, characterised in that the other end positioned outside the bone is slidingly accommodated in a receiving device, which receiving device is connected at an angle to a plate that can be fixed to a part of the broken hipbone, and in that the side that is positioned in the bone is fixed in the other part of the broken hipbone.

8. The medical device according to claim 7, characterised in that the side that is not positioned in the bone is slidingly accommodated in an opening of a pin which is placed in the intramedullary cavity of the upper leg.

9. The medical device for immobilising two bones connected by one or more joints, in particular vertebrae, according to claim 1, characterised in that the other end not positioned in the bone can be connected to stabilising elements, and wherein the first end that is positioned in the bone can be inserted into the pedicle of the vertebra.

* * * * *